(12) United States Patent
Johnston

(10) Patent No.: US 6,576,004 B2
(45) Date of Patent: Jun. 10, 2003

(54) WRAP-ONS AROMATIC THERMAL WRAPS

(75) Inventor: Scottia E. Johnston, Steilacoom, WA (US)

(73) Assignee: Weyerhauser Company, Federal Way, WA (US)

( * ) Notice: Subject to any disclaimer, the term of this patent is extended or adjusted under 35 U.S.C. 154(b) by 62 days.

(21) Appl. No.: 09/967,092

(22) Filed: Sep. 28, 2001

(65) Prior Publication Data
US 2002/0042641 A1 Apr. 11, 2002

Related U.S. Application Data
(60) Provisional application No. 60/238,368, filed on Oct. 6, 2000.

(51) Int. Cl.[7] .................................................. A61F 7/00
(52) U.S. Cl. .......................................... 607/114; 607/98
(58) Field of Search ......................... 607/114, 98; 2/15, 2/171.2; 604/359

(56) References Cited

U.S. PATENT DOCUMENTS

| | | | | |
|---|---|---|---|---|
| 3,211,146 A | * | 10/1965 | Rodelli ..................... 604/303 |
| 3,545,230 A | | 12/1970 | Morse | |
| 4,440,542 A | | 4/1984 | Foley | |
| 4,579,779 A | | 4/1986 | Ohno | |
| 4,585,797 A | * | 4/1986 | Cioca ....................... 604/303 |
| 4,897,297 A | | 1/1990 | Zafiroglu | |
| 4,961,493 A | | 10/1990 | Kaihatsu | |
| 5,129,391 A | | 7/1992 | Brodsky et al. | |
| 5,150,707 A | | 9/1992 | Anderson | |
| 5,243,708 A | * | 9/1993 | Vanuch ..................... 2/171.2 |
| 5,383,921 A | | 1/1995 | Barry | |
| 5,391,198 A | | 2/1995 | Cheney, III et al. | |
| 5,447,531 A | | 9/1995 | Wood | |
| 5,456,704 A | * | 10/1995 | Kilcullen ................... 607/111 |
| 5,569,683 A | | 10/1996 | Bootman et al. | |
| 5,731,083 A | | 3/1998 | Bahia et al. | |
| 5,769,833 A | * | 6/1998 | Hasse ...................... 604/359 |
| 5,951,534 A | * | 9/1999 | Cummings et al. ......... 604/359 |
| 5,976,547 A | | 11/1999 | Archer et al. | |
| 5,984,995 A | | 11/1999 | White | |
| 5,993,480 A | * | 11/1999 | Burrows .................... 607/114 |
| 6,004,345 A | | 12/1999 | Sudsina et al. | |
| 6,017,606 A | | 1/2000 | Sage et al. | |
| 6,020,040 A | | 2/2000 | Cramer et al. | |
| 6,048,326 A | | 4/2000 | Davis et al. | |
| 6,167,574 B1 | * | 1/2001 | Hayashida ................. 2/171.2 |
| 6,225,524 B1 | * | 5/2001 | Guarracino et al. ........ 604/359 |
| 6,409,746 B1 | * | 6/2002 | Igaki et al. ................ 607/109 |
| 2001/0021833 A1 | * | 9/2001 | Schmidt et al. ............ 604/359 |

FOREIGN PATENT DOCUMENTS

| | | | |
|---|---|---|---|
| JP | 2001-170096 | * | 6/2001 |
| JP | 2001-245915 | * | 9/2001 |

* cited by examiner

Primary Examiner—Linda C. M. Dvorak
Assistant Examiner—Jocelyn Ram
(74) Attorney, Agent, or Firm—Christensen O'Connor Johnston Kindness PLLC

(57) ABSTRACT

An aromatic thermal wrap comprises aromatic compounds such as camphor, menthol, essential oils and similar compounds, mixed with an absorbent material such as a silica powder and then combined with a superabsorbent polymer (SAP) to form a dry, aromatic mixture (200), and packaged in a flexible, water-permeable sachet (100). When suitably mixed with a silica powder, the aromatic compounds do not cause agglomeration or clumping of the superabsorbent polymer. Hydration of the sachet will cause the SAP to absorb water, forming a gel 210. The sachet may be produced with multiple pockets (110) that can be separated into single packets or into sets of packets to accommodate the specific application. The end user hydrates the sachet, and optionally heats or freezes the hydrated package, to produce an aromatic, thermal wrap.

13 Claims, 2 Drawing Sheets

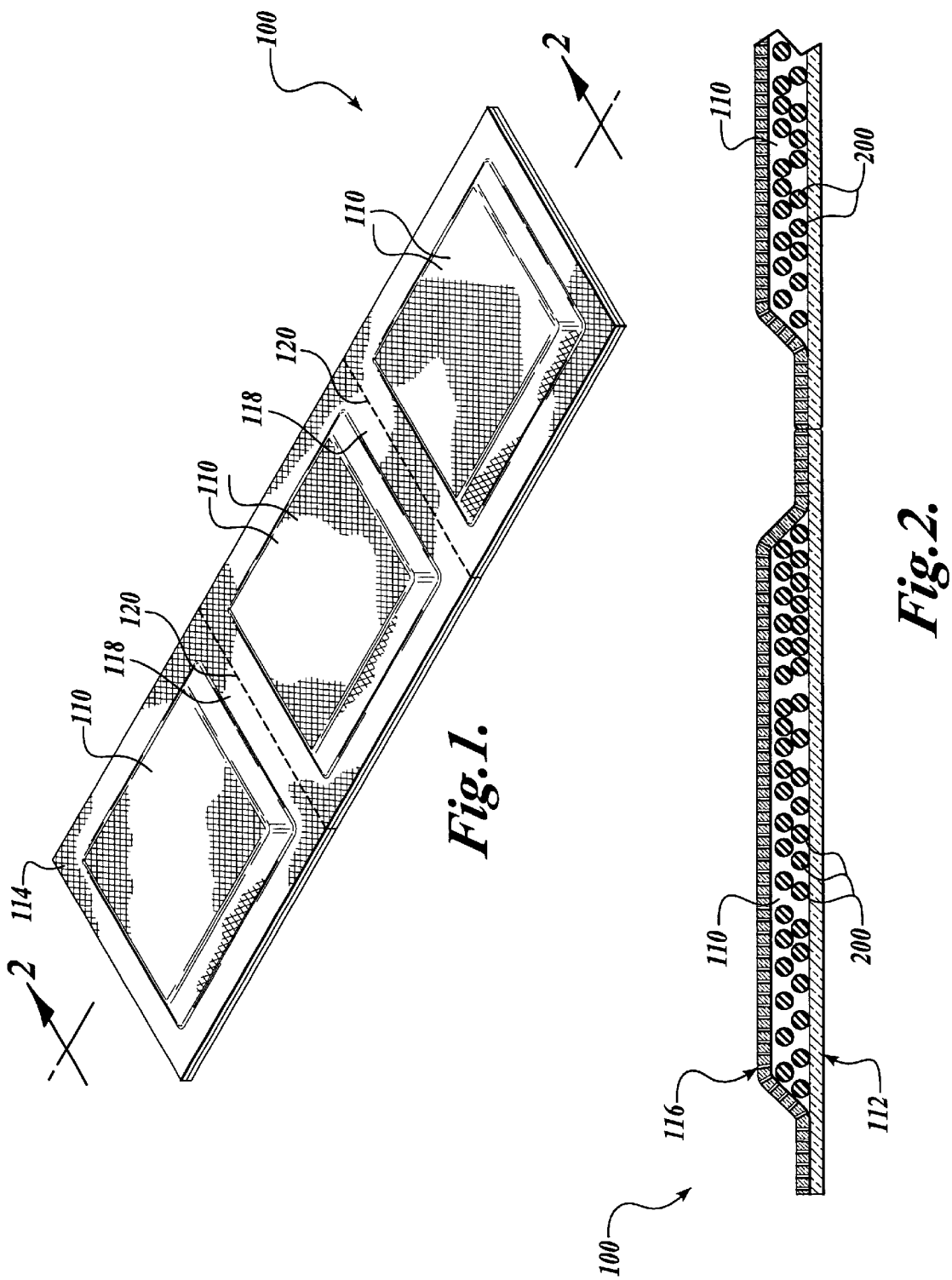

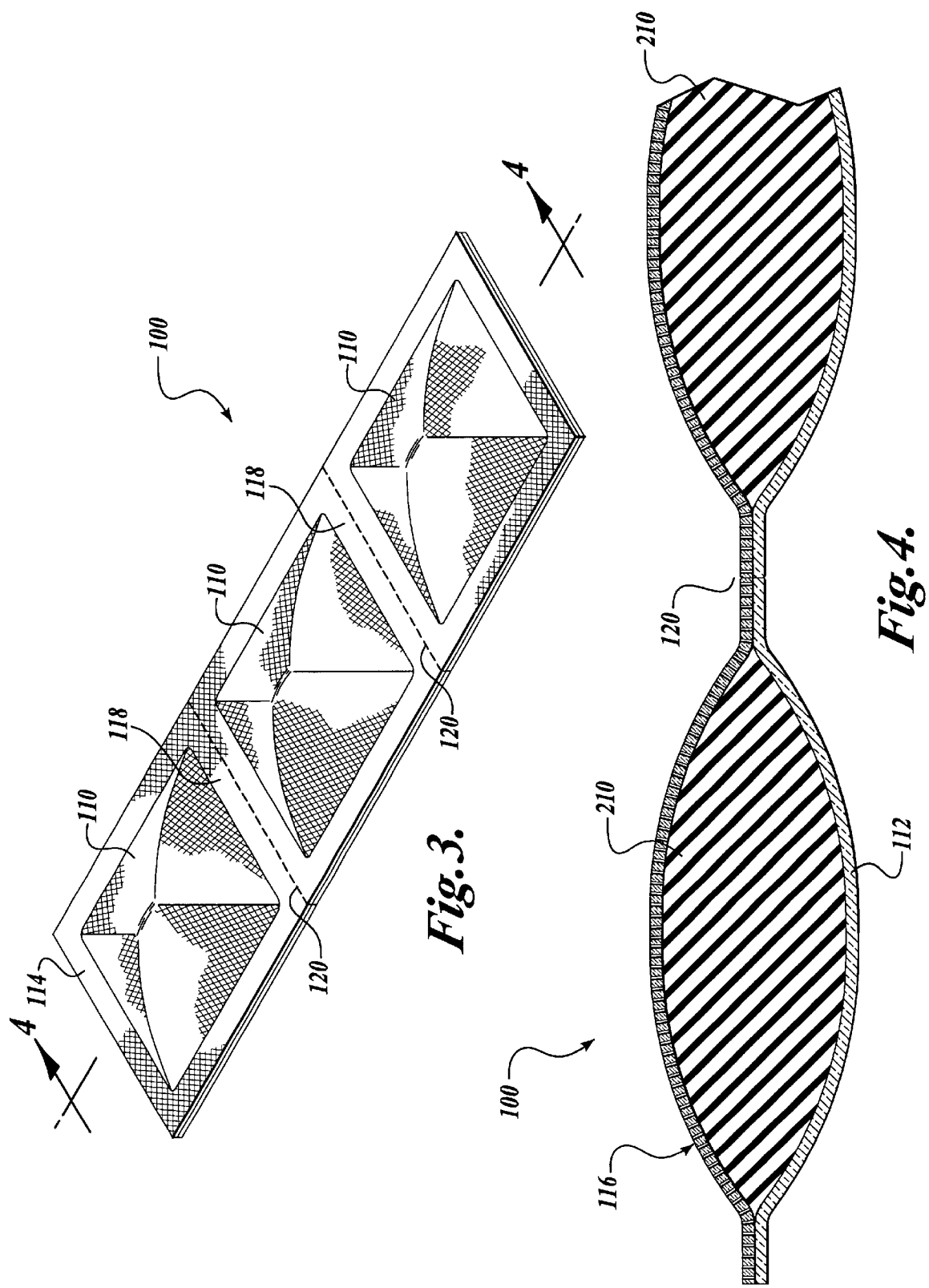

WRAP-ONS AROMATIC THERMAL WRAPS

CROSS-REFERENCE TO RELATED APPLICATION

This application claims the benefit of U.S. Provisional Patent Application No. 60/238,368, filed Oct. 6, 2000.

FIELD OF THE INVENTION

A method for producing a thermal wrap utilizing a superabsorbent polymer and, more particularly, a method for producing an aromatic thermal wrap that can be packaged in porous sachets as a dry, hydratable mixture that can be hydrated by the user and then chilled or heated prior to use.

BACKGROUND OF THE INVENTION

Superabsorbent polymers, including, but not limited to polymers such as polysaccharides, polyacrylates, and carboxymethylcellulose, are well known in the art for their ability to absorb many times their own weight, and sometimes hundreds of times their own weight, in water. The hydrated superabsorbent polymer typically forms a gel that substantially retains the thermal properties of water while simultaneously immobilizing the water in the gel material. Such gels are frequently used in thermal wraps that can be warmed, typically by heating the gel in a microwave oven or other warming device, or frozen by placing the thermal pack in a freezer.

Cold and hot thermal wraps are commonly used as a first treatment for minor injuries, such as sprains and bruises. The thermal wrap is applied directly to the injured area. Lowering the local body temperature near a minor injury during the first few hours after the injury occurs will cause the blood vessels to contract, and limit internal bleeding and swelling near the injury situs. After the body has repaired itself sufficiently to stop undesirable internal bleeding, typically approximately 24 hours after the injury occurred, application of heat to the injured region will cause the blood vessels expand, thereby increasing the flow of blood to the site of the injury, and speeding the healing process.

The application of heat is also a common method of treating temporary or chronic pain. Such therapeutic heat treatments are used for conditions that include general body aches, stiffness in muscles and joints, nerve pain, rheumatism, and the like. Generally, the afflicted area is warmed by applying a heating element such as a thermal wrap directly to the aching area.

A common type of thermal wrap is produced by hydrating a superabsorbent polymer (SAP) to create a gel, and encapsulating the gel in an impermeable, sealed, plastic container. For example, in U.S. Pat. No. 3,545,230, Morse discloses a flexible cooling device comprising an insoluble hydrophilic gel (made from, e.g., carboxymethylcellulose) sealed in a flexible packaging material that can be frozen. A disadvantage of sealing the gel in a package is that the product must be hydrated during manufacture. The hydrated product is much heavier and voluminous than the unhydrated polymer, and therefore shipping, storing, and displaying the hydrated product is more difficult.

In U.S. Pat. No. 6,017,606, Sage et al. discloses a reusable thermal compress wherein a superabsorbent polymer is disposed within a water permeable fabric. The water permeable fabric is gel retaining, and so the user can hydrate the compress immediately prior to use.

In some situations, it may provide additional physical and/or psychological benefit and comfort to the user of a thermal wrap to additionally experience a pleasant and/or therapeutic aroma when using the thermal wrap. In addition to potential therapeutic benefits that certain aromatics might provide, if a pleasant aroma enhances the user's enjoyment of the thermal wrap, then the user is likely to beneficially continue application of the thermal wrap for a longer period of time.

The use of aromatic compounds with a SAP is known in the art. In U.S. Pat. No. 4,961,493 to Kaihatsu, for example, an aromatic package is disclosed wherein an aromatic liquid or powder is dissolved in a solvent comprising 50 wt % ethanol and 50 wt % water, and then combined with a gelling agent, such as a SAP, and placed in a gas permeable and liquid impermeable package. Kaihatsu does not contemplate or suggest the use of the aromatic package as a thermal wrap, however. A disadvantage of the aromatic package disclosed by Kaihatsu is that the aromatic compound must be dissolved in a solvent (in the disclosure, a water/ethanol mixture) prior to combining the solvent/aromatic compound mixture with the gelling agent. Therefore, the aromatic package must be hydrated during manufacture, complicating the shipping, storing, and displaying requirements for the product. Moreover, many aromatics, particularly oil-based aromatics, are not dissolvable in water, thereby requiring the use of an alternative solvent such as ethanol.

It would be useful to mix a SAP with an aromatic compound (or a mixture thereof), that could by hydrated by the user just prior to use. It has been found, however, that if liquid aromatic compounds such as camphor, menthol, eucalyptus, essential oils, and/or aromatic oils are combined with a SAP gelling agent directly, without first hydrating the SAP, the superabsorbent polymer tends to agglomerate or clump together, thereby preventing or hindering the ability of the SAP to absorb water and form a gel.

SUMMARY OF THE INVENTION

An aromatic thermal wrap comprises a mixture of one or more liquid aromatic compounds that are absorbed and/or adsorbed into a porous silica powder and then mixed with a superabsorbent polymer. The mixture is placed in water permeable sachets. The aromatic thermal wrap can be manufactured, shipped, and stored without hydrating the superabsorbent polymer, thereby significantly simplifying handling of the product. The end-user hydrates the thermal wrap, and optionally heats or cools it prior to application, producing a thermal wrap that also provides a pleasant, and potentially health-promoting aroma.

In one embodiment of the invention, the thermal wrap sachets are produced in a regular planar array having individually separable pockets that can be utilized individually or in any convenient combination.

The aromatic compounds usable in accordance with the present invention include camphor, menthol, and essential oils. A carrier oil may be combined with the essential oils to moderate the intensity of the aroma.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1 is a perspective view of an embodiment of an aromatic thermal wrap according to the present invention;

FIG. 2 is a cross-sectional side view of the aromatic thermal wrap shown in FIG. 1 prior to hydration of the gel-forming aromatic mixture;

FIG. 3 is a perspective view of the aromatic thermal wrap shown in FIG. 1, after hydration of the gel-forming aromatic mixture; and FIG. 4 is a cross-sectional side view of the aromatic thermal wrap shown in FIG. 3 after hydration of the gel-forming aromatic mixture.

DETAILED DESCRIPTION OF THE PREFERRED EMBODIMENT

Referring to FIGS. 1 through 4, a preferred embodiment of an aromatic thermal wrap according to the present invention comprises a generally rectangular multi-compartment sachet 100 having a number of pockets 110. The sachet 100 is formed from a nonporous back panel 112 affixed generally at its edge portions 114 to a liquid- and gas-permeable but gel- and solid-retaining front panel 116. The back panel 112 and front panel 116 are also joined at a number of intermediate locations 118, thereby forming a sheet having a plurality of pockets 110. The back panel 112 and the front panel 116 may be affixed or joined in any of a number of means well known in the art, including but not limited to stitching, gluing, or heat bonding.

The back panel 112 and the front panel 116 may be made from any suitable materials that are capable of retaining a gel and are not damaged by soaking in water. Examples of suitable materials for the nonporous back panel 112 include, for example, polypropylene, polyester, or polyethylene films. Examples of suitable materials for the liquid- and gas-permeable front panel 116 include, for example, perforated or foraminous sheets made from polypropylene, polyester, polyethylene, and laminates thereof. The front panel 116 preferably has a number of pores or holes therethrough that are large enough to make the front panel 116 permeable to water and vapor, but small enough to substantially retain the aromatic gel-forming mixture 200 and the hydrated gel 210, and to prevent or at least hinder the gel 210 from leaking out of the sachet 100 when the thermal wrap is in use.

In the preferred embodiment, the sachet 100 is produced as a flexible sheet having a plurality of pockets 110 containing the aromatic mixture 200. Optionally, as shown in FIG. 1, the pockets 110 may be separated by perforations 120 or other zones of weakness in the intermediate portions 118, so that individual pockets 110, or a smaller set of pockets 110 may be separated to accommodate a particular application. It will be appreciated that although the illustrated preferred embodiment depicts a one-by-three array of pockets 110, the sachets could be produced in any convenient planar array of pockets, including, for example, a large roll of pockets one wide by many long, or a sheet of pockets many wide by many long. Virtually any reasonably sized pocket may be produced, and in particular, a composite sachet utilizing a number or pockets with differing dimensions could be utilized to accommodate particular applications.

Prior to final sealing or joining of the edge portion 114, a quantity of a gel-forming aromatic mixture 200 is inserted into each pocket 110, the aromatic mixture 200 comprising one or more aromatic compounds that have been absorbed into a fine silica powder and a superabsorbent polymer (SAP). As used herein, a "superabsorbent polymer" refers to a polymeric material that is capable of absorbing large quantities of fluid by swelling and forming a hydrated gel (i.e., a hydrogel). In addition to absorbing large quantities of fluids, superabsorbent materials can also retain significant amounts of bodily fluids under moderate pressure.

Superabsorbent polymers generally fall into three classes: starch graft copolymers, cross-linked carboxymethylcellulose derivatives, and modified hydrophilic polyacrylates. Examples of such superabsorbent polymers include hydrolyzed starch-acrylonitrile graft copolymers, neutralized starch-acrylic acid graft copolymers, saponified acrylic acid ester-vinyl acetate copolymers, hydrolyzed acrylonitrile copolymers or acrylamide copolymers, modified crosslinked polyvinyl alcohol, neutralized self-crosslinking polyacrylic acids, crosslinked polyacrylate salts, carboxylated cellulose, and neutralized crosslinked isobutylene-maleic anhydride copolymers.

SAPs are available commercially, for example, polyacrylates from Clariant of Portsmouth, Va. These superabsorbent polymers come in a variety of sizes, morphologies, and absorbent properties (available from Clariant under trade designations such as IM 3500 and IM 3900). Other SAPs are marketed under the trademarks SANWET (supplied by Sanyo Kasei Kogyo Kabushiki Kaisha), and SXM77 (supplied by Stockhausen of Greensboro, N.C.). Still other SAPs are described in U.S. Pat. No. 4,160,059; U.S. Pat. No. 4,676,784; U.S. Pat. No. 4,673,402; U.S. Pat. No. 5,002,814; U.S. Pat. No. 5,057,166; U.S. Pat. No. 4,102,340; and U.S. Pat. No. 4,818,598—all expressly incorporated herein by reference. Products such as diapers that incorporate SAPs are described in U.S. Pat. No. 3,699,103 and U.S. Pat. No. 3,670,731. In the preferred embodiment of the present invention, a polysaccharide SAP is used.

As seen most clearly by comparing FIG. 2, showing a cross-sectional view of the non-hydrated sachet 100, with FIG. 4, showing a cross-sectional view of the hydrated sachet 100, the pockets 110 are sized to permit expansion of the aromatic mixture 200 upon absorption of water to form a gel 210. Modem SAPs may absorb ten to a hundred or more times their weight in water, and so the pockets 110 must be large enough to accommodate the fully hydrated aromatic mixture 200 without causing the pockets to burst.

Most aromatic compounds are hydrophobic, and are frequently formulated in organic hydrocarbon bases or carrier oils. These compounds are not water soluble and, when mixed with a typical, unhydrated SAP, will cause undesirable clumping, which reduces the ability of the SAP to absorb water and form a gel. Thus the present invention uses an inert, absorbent compound, such as a porous silica powder, to absorb the aromatic compounds before mixing with the SAP. Although a porous silica powder is used in the preferred embodiment, it should be apparent that other inert absorbent compounds may also be used, including, for example, fine, porous, synthetic polymer particles such as clay, and zeolytes. A porous silica powder is generally less expensive than synthetic polymer particles, and more aesthetically appealing, and less prone to staining than zeolytes, however.

According to the present invention, the aromatic compounds are first absorbed into a porous silica powder at a sufficiently low loading that the aromatic compound/silica powder can be handled essentially as a powder. As used herein, "absorb" means the process of one substance taking up the matter of another substance, and so shall include without limitation, where appropriate, adsorption and/or absorption of one material by another. The impregnated silica powder can be mixed with a SAP without causing it to clump and without significantly interfering with the ability of the SAP to absorb water and form a gel. The preferred silica powder is 70 to 200 or 200 to 400 mesh size (corresponding to particle sized approximately 0.0015" to 0.0083" in diameter), and more preferably, 70 to 200 mesh size. A typical characteristic pore size in a suitable silica powder is about 60 Angstrom.

The dry mixture of aromatic compound/silica powder and SAP can therefore be sealed into the sachet pockets 110 without hydrating the SAP. The resulting sachets 100 can be easily packaged, stored, transported, displayed, and otherwise handled prior to delivery to the final user.

An aromatic product, such as the aromatic thermal wrap of the present invention, must generally be packaged for display in a manner that will not interfere with other neighboring products. In particular, the aromatic thermal wrap will generally be sealed in a package such that the scent from the aromatic compounds does not undesirably permeate the point of display. The sealed package will also hinder the vaporization of the volatile compounds, providing the product with a longer shelf life and protecting the thermal wrap from external damaging factors such as ultraviolet rays. Because the SAP can absorb ten to a hundred or more times its own weight in water, it will be appreciated that the ability to mix and package the unhydrated aromatic compound with the SAP for later use will greatly simplify the packaging and handling of the product.

When the sachet 100 is required for use as a thermal wrap, it can be soaked in water to hydrate the SAP, forming an aromatic gel 210. The resulting gel 210 retains approximately the thermal properties of the absorbed water and the sachet 100 may be heated, as in a microwave oven, or frozen, depending on the desired application, prior to use. It has been found that the aromatic compounds in the gel 210 will evaporate over time, providing the thermal wrap of the present invention with the desired aromatic properties.

Specific formulae for the mixture of aromatic compounds that are absorbed into the silica powder can be tailored to produce a plethora of pleasant and potentially healthful scents. A non-aromatic carrier oil can be mixed with the aromatic compounds to moderate the intensity of the gel scent. In the preferred embodiment, the ratio of aromatic compounds, including the carrier oil, if any, to the silica powder, is preferably maintained in the range of 1:1 to 1:2, and more preferably approximately 1:1.5. This range of loading of the aromatic compounds into the silica has been found to maintain powder-like behavior in the impregnated silica while also enabling sufficient aromatic compounds to be incorporated in the gel 210 to produce the desired intensity of the aroma.

Although the preferred ratio of SAP to the aromatic compound and silica mixture will vary depending on the specific SAP that is used, as well as the selected aromatic compounds and desired intensity of the scent, when using a polysaccharide SAP, the SAP may be approximately 75 to 90 wt % of the mixture of aromatic compound/silica powder and SAP, and most preferably about 80 to 83 wt %.

EXAMPLE 1

In one embodiment of the present invention, the aromatic mixture 200 includes a polysaccharide SAP, silica, menthol, and camphor in the following proportions:

i) SAP, preferably 79 wt % to 87.5 wt %, most preferably 82.7 wt %;

ii) silica, preferably 7 wt % to 10 wt %, most preferably 10 wt %;

iii) l-menthol, preferably 4 wt % to 8 wt %, most preferably 5.5 wt %; and iv) d-camphor, preferably 1.5 wt % to 3 wt %, most preferably 1.8 wt %.

EXAMPLE 2

In another embodiment, utilizing essential oils, the aromatic mixture includes approximately 80 wt % SAP, 12 wt % silica, and 8 wt % of essential oils including any carrier oil. Many different formulations of essential oils that have been found to produce pleasant scents, including:

Mix I: Atlas Cedarwood, Rosemary, Mandarin Lime, Nutmeg, Lavandin;

Mix II: Atlas Cedarwood, Benzoin, Guaiacwood, Rosemary, Sweet Birch, Scotch Pine, Silver Fir Needles;

Mix III: Atlas Cedarwood, Elemi, Ginger; and

Mix IV: Grapefruit, Jasmine, Sandalwood.

While the preferred embodiment of the invention has been illustrated and described, it will be appreciated that various changes can be made therein without departing from the spirit and scope of the invention.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for producing an aromatic thermal wrap comprising:
   a. mixing a liquid aromatic compound with an inert absorbent compound;
   b. placing said mixture and an unhydrated superabsorbent polymer in a gel-retaining, gas permeable, closable sachet; and
   c. closing said sachet.

2. The method of claim 1 further comprising the step of sealing said sachet in a removable, gas impermeable wrapper.

3. The method of claim 1 wherein said inert absorbent compound is a porous silica powder.

4. An hydratable composition for an aromatic thermal wrap comprising:
   a. from about 75% to about 90% by weight of a superabsorbent polymer;
   b. from about 3% to about 12.5% by weight of an aromatic compound and carrier oil; and
   c. from about 5% to about 17% by weight of an inert absorbent compound;
   wherein said aromatic compound is absorbed into said inert absorbent compound prior to combining said aromatic compound and said inert absorbent compound with said superabsorbent polymer.

5. The hydratable composition of claim 4 wherein said inert absorbent compound is a porous silica powder.

6. The hydratable composition of claim 4 wherein said superabsorbent polymer is selected from the group consisting of polysaccharides, polyacrylates, and carboxymethylcellulose.

7. The hydratable composition of claim 4 wherein said aromatic compound is selected from the group consisting of camphor, menthol, eucalyptus, essential oils, aromatic oils, and fragrance oils.

8. The hydratable composition of claim 4 wherein said aromatic compounds comprise a mixture of compounds selected from the group consisting of camphor, menthol, eucalyptus, essential oils, aromatic oils, and fragrance oils.

9. An aromatic thermal wrap comprising a porous sachet containing a mixture that includes an inert absorbent material containing an absorbed aromatic compound and a superabsorbent polymer.

10. The aromatic thermal wrap of claim 9 wherein said inert absorbent material is a porous silica powder.

11. The aromatic thermal wrap of claim 9 wherein said aromatic compound comprises a mixture of compounds selected from the group consisting of camphor, menthol, eucalyptus, essential oils, aromatic oils, and fragrance oils.

12. The aromatic thermal wrap of claim 9 wherein said porous sachet comprises a plurality of separable pockets, said pockets being formed from a porous front panel and a nonporous back panel.

13. The aromatic thermal wrap of claim 9 wherein the porous sachet comprises a flexible, nonporous, water-tolerant back panel adhered to a liquid- and gas-permeable front panel, and wherein said back panel and said front panel cooperatively form a plurality of pockets for containing said mixture.

* * * * *